(12) United States Patent
McNally

(10) Patent No.: US 9,717,622 B2
(45) Date of Patent: Aug. 1, 2017

(54) SPLINT ASSEMBLY AND SYSTEM

(71) Applicant: Schoolhouse Medical Equipment, Inc., Fuquay Varina, NC (US)

(72) Inventor: Michael L. McNally, Fuquay Varina, NC (US)

(73) Assignee: SCHOOLHOUSE MEDICAL EQUIPMENT, INC., Fuquay Varina, NC (US)

( * ) Notice: Subject to any disclaimer, the term of this patent is extended or adjusted under 35 U.S.C. 154(b) by 158 days.

(21) Appl. No.: 14/523,289

(22) Filed: Oct. 24, 2014

(65) Prior Publication Data

US 2015/0119776 A1    Apr. 30, 2015

Related U.S. Application Data

(60) Provisional application No. 61/961,831, filed on Oct. 24, 2013.

(51) Int. Cl.
*A61F 5/052* (2006.01)
*A61F 5/058* (2006.01)
*A61F 5/05* (2006.01)

(52) U.S. Cl.
CPC ............ *A61F 5/058* (2013.01); *A61F 5/05* (2013.01); *A61F 5/0585* (2013.01); *A61F 5/05841* (2013.01); *A61F 5/05858* (2013.01); *A61F 5/05883* (2013.01); *A61F 2250/0007* (2013.01)

(58) Field of Classification Search
CPC .. A61F 5/00; A61F 5/01; A61F 5/0104; A61F 5/0106; A61F 5/04; A61F 5/05; A61F 5/058; A61F 5/05825; A61F 5/05841; A61F 5/0585; A61F 5/05858; A61F 5/05883
USPC ............ 602/5, 12, 19, 20, 23; 128/869, 870, 128/878, 882

See application file for complete search history.

(56) References Cited

U.S. PATENT DOCUMENTS

| | | | |
|---|---|---|---|
| 6,719,711 B1 * | 4/2004 | Islava | A61F 5/05816 128/DIG. 20 |
| 8,029,426 B2 * | 10/2011 | Sohn | A63B 23/0211 482/140 |
| 8,622,944 B1 * | 1/2014 | Villahermosa | A61F 5/05825 128/870 |
| 9,226,841 B1 * | 1/2016 | Amodt | A61F 5/0102 |

* cited by examiner

*Primary Examiner* — Keri J Nelson
(74) *Attorney, Agent, or Firm* — Christopher J. Knors; Moore & Van Allen, PLLC

(57) ABSTRACT

A splint assembly comprising a first section with at least one compartment and one or more rigid members positioned within the at least one compartment, the one or more rigid members providing a rigid dimensional axis and at least one flexible dimensional axis; and at least one second section configured to couple with the first section, the at least one second section comprising at least one compartment and one or more rigid members positioned within the at least one compartment, so that the at least one second section has a rigid dimensional axis and at least one flexible dimensional axis; and at least one attachment member is operatively coupled to the at least one second section.

18 Claims, 6 Drawing Sheets

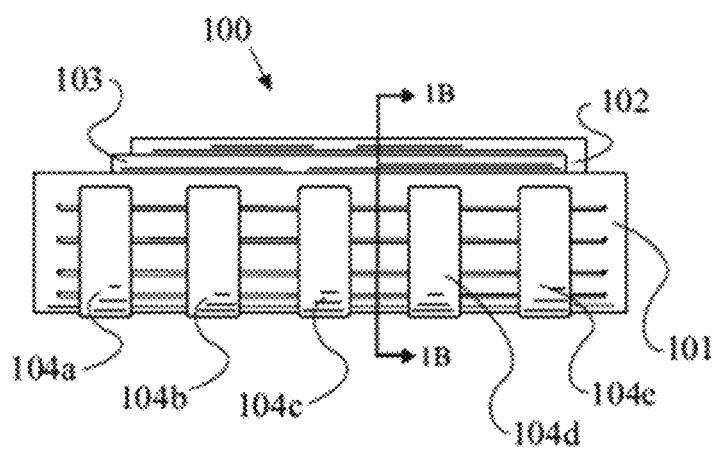
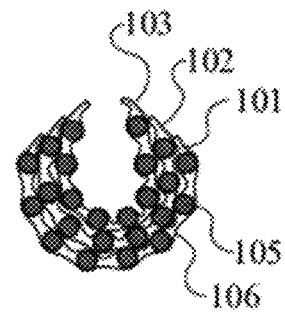
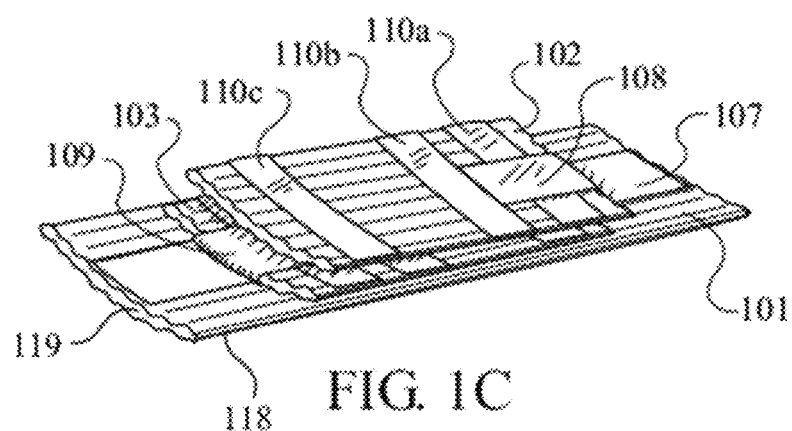
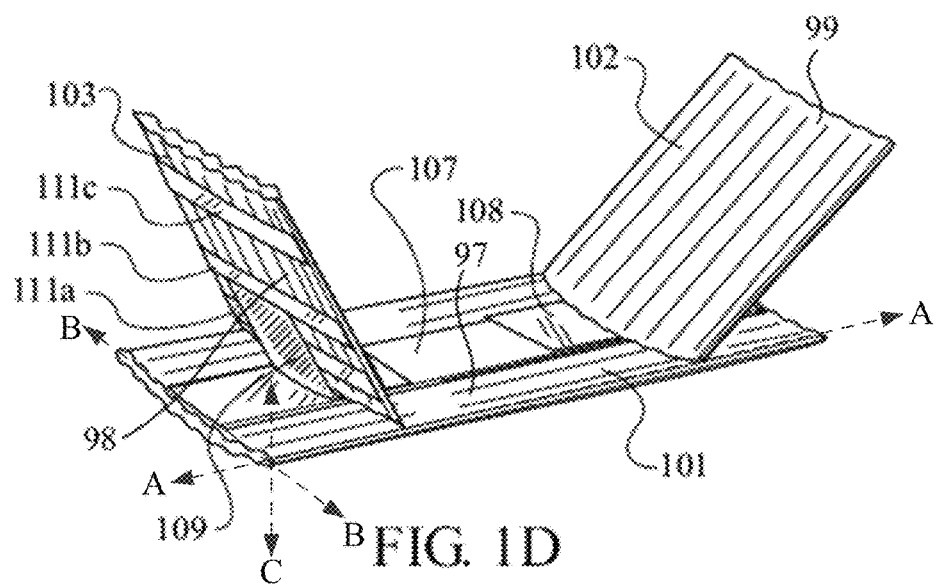

SPLINT ASSEMBLY AND SYSTEM

CROSS-REFERENCE TO RELATED APPLICATIONS

This application claims the benefit of U.S. Provisional Application No. 61/961,831, filed Oct. 24, 2013, which is incorporated by reference in its entirety.

TECHNICAL FIELD

The present disclosure relates to a splint assembly having a first section comprising a rigid dimensional axis and at least one flexible dimensional axis; and at least one second section comprising a rigid dimensional axis and at least one flexible dimensional axis, and an attachment member operatively coupled to the at least one second section.

BACKGROUND

This assembly relates to the immobilization of broken bones at the scene of injury to facilitate removal of the patient from the scene. Broken bones are a very common injury for people, resulting from many kinds of trauma. First responder medical specialists, when arriving at the scene of an accident, may encounter broken bones or suspected broken bones in the feet, legs, pelvis, back, arms, or neck of the accident victim, or breaks in multiple locations. As the first responder, the medical specialist may have no advance information about the type, severity, or location of broken bones. The first step in treating a broken bone is to immobilize the break, which is typically done by fixing an rigid member to uninjured points above and below the break and immobilizing the joints above and below the suspected fracture, in a process commonly known as splinting. It is important for a first responder to have rapid access to the appropriate materials to carry out the splinting process to treat such victims in preparation for removing them from the site of the accident. This can be challenging if the first responder is working in a remote area and only has access to supplies that they are able to carry with them.

SUMMARY

In a first embodiment, a splint assembly is provided. The splint assembly comprising a first section comprising a top surface, an opposing bottom surface separated from the top surface by a peripheral edge, the peripheral edge comprising a pair of longitudinal edges and a pair of cross-sectional edges. At least one compartment is positioned between the top surface and the bottom surface generally aligned with the longitudinal edges, and one or more rigid members are positioned within the at least one compartment, the one or more rigid members generally aligned with the longitudinal edges so that the first section has a rigid dimensional axis and at least one flexible dimensional axis. The splint assembly further comprises at least one second section configured to couple with the first section, each of the at least one second section comprising a top surface, an opposing bottom surface separated from the top surface by a peripheral edge; the peripheral edge comprising a pair of longitudinal edges and a pair of cross-sectional edges. At least one compartment is positioned between the top surface and the bottom surface generally aligned with the longitudinal edges and one or more rigid members are positioned within the at least one compartment, the one or more rigid members generally aligned with the longitudinal edges so that the at least one second section has a rigid dimensional axis and at least one flexible dimensional axis. At least one attachment member having a first end and a second end is operatively coupled to at least one of the pair of cross-sectional edges and configured for coupling with the top or the bottom surface of the first surface of the first section or another of the at least one second sections. Whereby the combination of the first section and the at least one second section provides a splint assembly having a rigid dimensional axis and at least one flexible dimensional axis.

In an aspect of the first embodiment, the at least one attachment member is fixedly coupled at the first or the second end to at least one of the pair of cross-sectional edges of the at least one second section and reversibly coupled to the top or the bottom surface of another one of the first section or another of the at least one second sections.

In another aspect, alone or in combination with any of the previous aspects of the first embodiment, the attachment members of two of the at least one second section are coupled to the same surface of the first section. In another aspect, alone or in combination with any of the previous aspects of the first embodiment, the rigid dimensional axis of the one or more second section is configure to articulate about the attachment member between an angle of zero to 180 degrees relative to the rigid dimensional axis of the first section.

In another aspect, alone or in combination with any of the previous aspects of the first embodiment, the attachment members of two of the at least one second section are coupled to the proximity of the opposing cross-sectional edges of the first section to provide an extended elongated structure consisting of the first and the two of the one or more second sections. In another aspect, alone or in combination with any of the previous aspects of the first embodiment, the attachment members of two or more of the one or more second sections are coupled in proximity to opposing cross-sectional edges of two or more of the second section.

In another aspect, alone or in combination with any of the previous aspects of the first embodiment, the first section comprises a number of the rigid members less than that of the one or more second sections. In another aspect, alone or in combination with any of the previous aspects of the first embodiment, the at least one of the rigid members of the first section are of a diameter and/or length that is different than at least one of the one or more second sections.

In another aspect, alone or in combination with any of the previous aspects of the first embodiment, the extended elongated structure of elongated flexible sections is of a length corresponding to that of at least a portion of a human arm, or of a length corresponding to that of at least a portion of a human leg, or of a length corresponding to that of at least a portion of a human spine.

In another aspect, alone or in combination with any of the previous aspects of the first embodiment, the splint assembly further comprises one or more elongated strap members, each of the strap members having fastening means at opposing ends thereof, the fastening means reversibly couplable to the top or the bottom surface of the first section and/or the at least one second section.

In a second embodiment, a method of manufacturing a splint assembly is provided. The method comprising providing a first section comprising: a top surface; an opposing bottom surface separated from the top surface by a peripheral edge; the peripheral edge comprising a pair of longitudinal edges and a pair of cross-sectional edges; and forming at least one compartment positioned between the top surface and the bottom surface generally aligned with the longitudinal edges; the at least one compartment configured to receive or more rigid members generally aligned with the longitudinal edges so that the first section has a rigid dimensional axis and at least one flexible dimensional axis. The method further comprises providing at least one second section configured to operatively couple with the first section, each of the at least one second section comprising: a top surface; an opposing bottom surface separated from the top surface by a peripheral edge; the peripheral edge comprising a pair of longitudinal edges and a pair of cross-sectional edges; forming at least one compartment positioned between the top surface and the bottom surface generally aligned with the longitudinal edges; the at least one compartment configured to receive or more rigid members generally aligned with the longitudinal edges so that the first section has a rigid dimensional axis and at least one flexible dimensional axis; and providing at least one attachment member having at least one end operatively coupled to at least one of the pair of cross-sectional edges and configured for coupling with the first section or another of the at least one second sections. Whereby the first section and the at least one second section is configurable as a splint assembly having a rigid dimensional axis and at least one flexible dimensional axis.

In an aspect of the second embodiment, the at least one attachment member is fixedly coupled at the first or the second end to at least one of the pair of cross-sectional edges of the at least one second section and reversibly coupled to the top or the bottom surface of another one of the first section or another of the at least one second sections.

In another aspect, alone or in combination with any of the previous aspects of the second embodiment, the at least one compartment is configured to be reversibly sealed with the one or more rigid member or irreversibly sealed with the one or more rigid member.

In another aspect, alone or in combination with any of the previous aspects of the second embodiment, the rigid dimensional axis of the one or more second section is configure to articulate about the fastening means between an angle of zero to 180 degrees relative to the rigid dimensional axis of the first section. In another aspect, alone or in combination with any of the previous aspects of the second embodiment, the fastening members of two of the at least one second section are coupled to the proximity of the opposing cross-sectional edges of the first section to provide an extended elongated structure consisting of the first and the two of the one or more second sections.

In another aspect, alone or in combination with any of the previous aspects of the second embodiment, the at least one rigid member is a rod, sheet, or strip of material.

In another aspect, alone or in combination with any of the previous aspects of the second embodiment, the method further comprises providing one or more elongated strap members, each of the strap members having fastening means at opposing ends thereof, the fastening means configured for reversibly coupling to the top or the bottom surface of the first section and/or the at least one second section.

In a third embodiment, splint assembly is provided. The splint assembly comprising a first section comprising at least one compartment positioned between a top surface and a bottom surface, and one or more rigid members positioned within the at least one compartment, so that the first section has a rigid dimensional axis and at least one flexible dimensional axis. The splint assembly further comprising at least one second section configured to couple with the first section comprising: at least one compartment positioned between a top surface and a bottom surface, one or more rigid members positioned within the at least one compartment so that the at least one second section has a rigid dimensional axis and at least one flexible dimensional axis, and at least one attachment member operatively couplable to the first section or another of the at least one second sections, wherein the combination of the first section and the at least one second section provides a splint assembly having a rigid dimensional axis and at least one flexible dimensional axis. In one aspect, the rigid member is a rod, sheet, or strip of material. In other aspect, the splint assembly further comprises one or more elongated strap members, each of the strap members having fastening means at opposing ends thereof, the fastening means reversibly couplable to the first section and/or the at least one second section.

BRIEF DESCRIPTION OF THE DRAWINGS

FIG. 1A is a front view of an exemplary splint system device embodiment as disclosed and described herein.

FIG. 1B is an end-section view of the splint system as shown in FIG. 1A.

FIG. 1C is a perspective view of the splint system as shown in FIG. 1A shown lying flat in a compact position.

FIG. 1D is a perspective view of the splint system as shown in FIG. 1A showing additional second sections rotated away from the first section.

DETAILED DESCRIPTION

Figure 2A:
FIG. 2A is a front view of attachment members as disclosed and described herein.

The disclosure described herein addresses requirements described above. The splint assembly is a compact and lightweight configuration for portability, provides an inflexible support and means of quickly and simply fixing the support to the patient, and is configured to be quickly and easily adjusted to a variety of potential injuries. These and other objects, aspects and features of the present disclosure will be better understood from the following detailed description of the preferred embodiment when read in conjunction with the appended drawing figures.

FIG. 1A depicts a front view of a splint system (100) arranged in a compact configuration, comprising a main section (101) (hereinafter also referred to as "first section"). First section (101) can be configured in a variety of shapes. As shown, first section (101) is shown as a generally rectangular shape, having a pair of longitudinal edges and corresponding cross-sectional edges, providing up of a plurality of compartments (106). Other configurations of the splint system (100) include oval or square shapes. One or more additional sections (102) and (103) (hereinafter collectively also referred to as "at least one additional section") are shown folded inwards onto the first section (101) in a folded state suitable for transport or storage.

FIG. 1B is an end-section view along sectional plane 1B-1B of the splint assembly (100) showing first section (101) and additional sections (102 and 103). At least one substantially inflexible member (105) (hereinafter also referred to as "rigid member") can be seen each enclosed in one or more compartments (106). The term "rigid member" is inclusive of a material configuration and/or structure that is substantially rigid or inflexible in at least one dimension but can be at least partially flexible in another, different dimension (height, width, or length "H×W×L" dimension). For example, a dowel or sheet of rigid plastic or metal is an example of a rigid member, which is essentially inflexible in its diameter or H×W dimensions, but could flex, wrap, or conform along its longitudinal axis "L" dimension about a body part with the proper selection of material and dimension parameters, which selection of such parameters are within the skill of one in the art.

With reference to FIG. 1C, the at least one rigid member 105 is essentially parallel to the longitudinal (118) and essentially perpendicular to cross-sectional edge (119). In at least one aspect, fabric of the splint assembly (100) can be constructed of a material that is flexible and/or elastic. Suitable materials for the rigid member include thermoplastics, engineering plastics, for example nylon, polypropylene, reinforced polypropylene, polyester, or blends thereof. In other aspects, wood, plastic, or metal dowels can be used.

Optional Straps elements (104a, 104b, 104c, 104d, and 104e), for example, of a hook functional material are configured to receive a loop containing strip discussed below, are shown, are configured on one or more surfaces of the first or additional sections (101), (102), (103) and are arranged substantially perpendicular to the longitudinal axis of rigid members (105).

FIG. 1C is a perspective view of the first section (101) and the additional sections (102 and 103) lying flat in the compact position. A strip of loop connector material (107) is fixed to the central length of the first section (101). The additional section (102) is fixed to the first section (101) by the strip of hook connector material (108) and the additional section (103) is fixed to the first section (101) by the strip of hook connector material (109). Strips of hook connector material (110a, 110b, and 110c) are fixed to the surface of the additional section (102) perpendicular to the inflexible axis.

FIG. 1D is a perspective view of the additional sections (102, 103) rotated away from the first section (101). First section (101) is shown with at least one rigid dimensional axis corresponding to the longitudinal axis A of the first section. First section (101) can flex or wrap in and/or out of a plane defined with dimensional axes A and B, or A and C so as to conform or at least partially wrap around a body part or for storage, but substantially cannot flex or wrap in/out a plane defined by B and C (e.g., perpendicular to axis A, "the rigid dimensional axis"). Likewise, axes A, B, and C of second sections (102, 103) (not shown) are similarly arranged and second sections have similar flex/wrap functionality. Loop connector material (107) of first section (101) fixedly attaches additional sections (102, 103) on surface (97) via hook connector material strips (108 and 109). As shown perpendicular to the inflexible axis of the rigid members (105) of additional section (103), are three strips of loop connector material (111a, 111b, and 111c). In other aspects, less than 3 strips of loop connector material can be used. In other aspects, more than 3 strips of loop connector material can be used.

FIG. 2A is a front view of the attachment straps (112) that in certain aspects function as fastening means to secure the arrangement of the first section (101) and the one or more second sections (102 and/or 103) about the appendage or body. In one aspect, a plurality of attachment straps (112) can be employed. In another aspect, a single attachment strap (112) can be used. The attachment straps (112) can be flexible and/or elastic. In one aspect, the attachment straps (112) can be elongated strips.

Figure 2B:
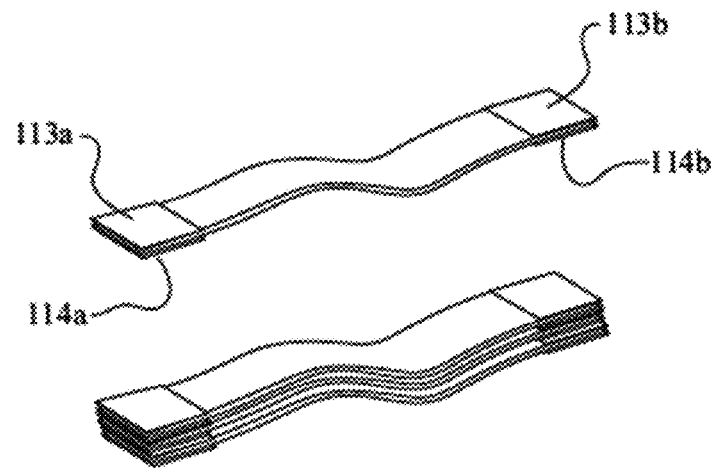
FIG. 2B is a perspective view of the attachment members of FIG. 2A as disclosed and described herein.

FIG. 2B is a perspective view of the attachment straps (112) with an exemplary hook connector material (113a and 113b) on one side of each end and loop connector material (114a and 114b) on each end of the other side. Hook and loop connector material can be configured as VELCRO™ or other suitable and/or similar functional components or pair of components, such as a buckle, snap assembly, a button/button hole or other male-female connector assembly. In one aspect, a pressure sensitive adhesive (PSA) on one or both surfaces of the sections (101, 102, 103) and/or strap (112) can be used to secure the splint assembly to the subject.

Figure 2C:
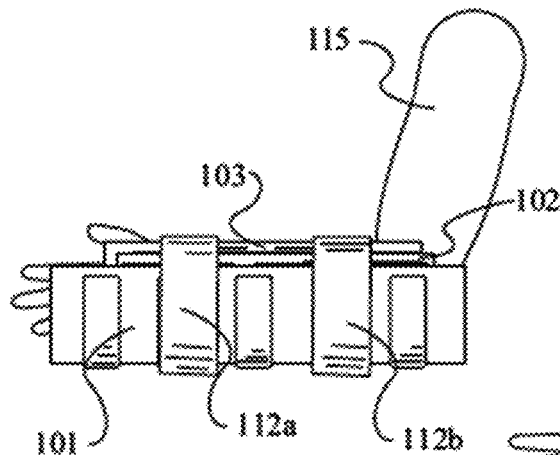
FIG. 2C is a side view of the first section with the additional second sections deployed on an arm as disclosed and described herein.

FIG. 2C is a side view of the first section (101) with the additional sections (102 and 103) fixed as shown and utilized for a portion of an arm (115) (and may include the wrist) with straps (112a and 112b).

Figure 2D:
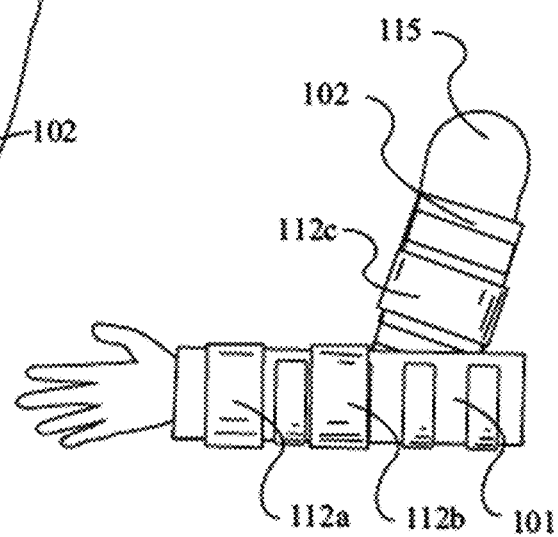
FIG. 2D is a side view of the first section with the additional second section of the embodiment depicted in FIG. 1A, disposed at an angle with straps so as to support an elbow of a subject in need thereof, as disclosed and described herein.

FIG. 2D is a side view of the first section (101) with the additional section (102) fixed at an angle with straps (112a, 112b, and 112c) to support an elbow and/or a portion of arm (115) and/or wrist as shown. The splint assembly, as shown, can be configured to secure the upper and lower arm segments in a variety of angles as needed.

Figures 3A, 3B:
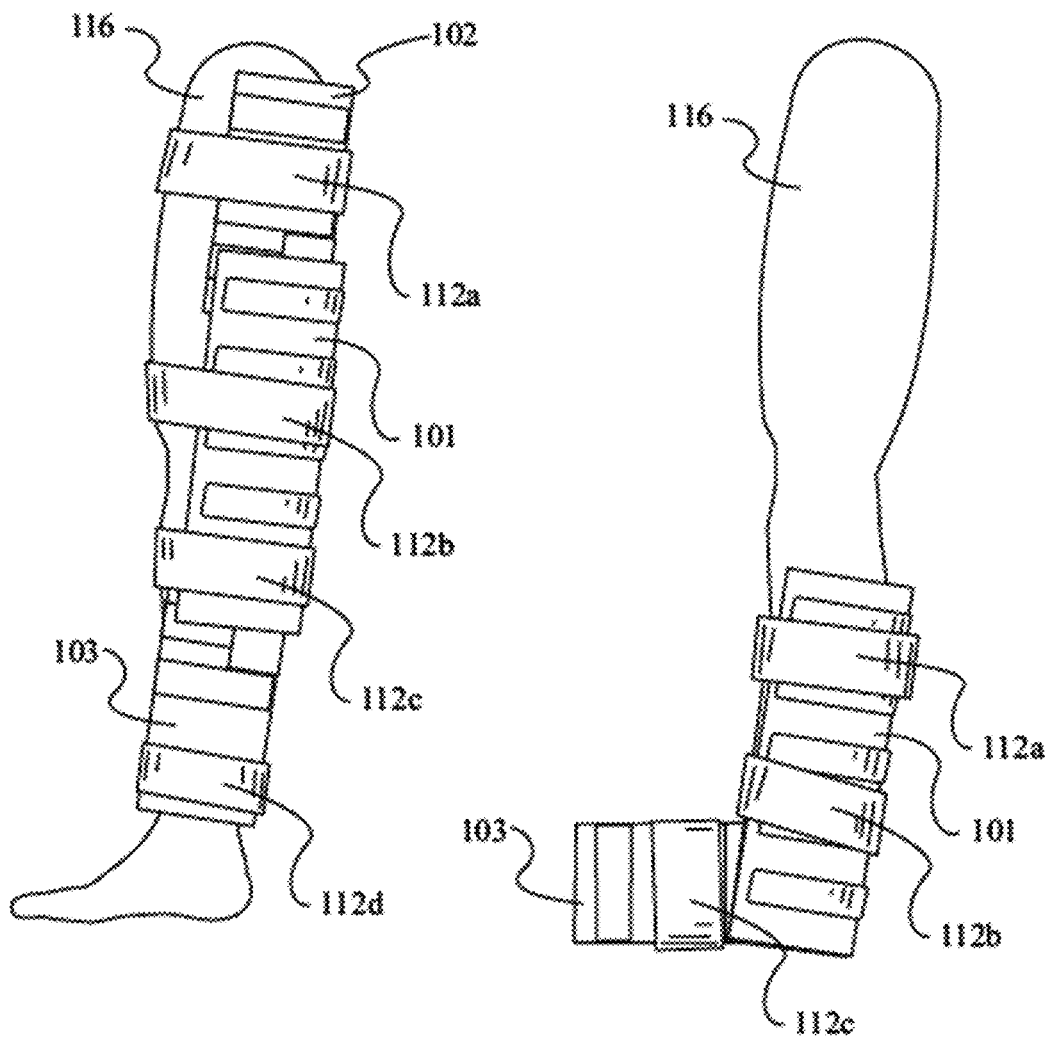
FIG. 3A is a side view of the first section with the additional second section of the embodiment depicted in FIG. 1A, deployed at one hundred and eighty degrees so as to support a leg of a subject in need thereof, as disclosed and described herein.
FIG. 3B is a side view of the first section with the additional second section of the embodiment depicted in FIG. 1A, deployed at an angle so as to support an ankle of the subject in need thereof, as disclosed and described herein.

FIG. 3A is a side view of the first section (101) and the additional sections (102 and 103) deployed at one hundred and eighty degrees and held in place by straps (112a, 112b, 112c, and 112d) shown being utilized on a leg (116). The splint assembly, as shown, can be configured to secure the upper and lower leg segments in a substantially a straight line as needed.

FIG. 3B is a side view of the first section (101) and the additional section (103) fixed at an angle with straps (112a, 112b, and 112c) to support the ankle shown being utilized on a leg (116). The splint assembly, as shown, can be configured to secure the upper and lower leg segments and/or ankle in a variety of angles as needed.

Figure 4:
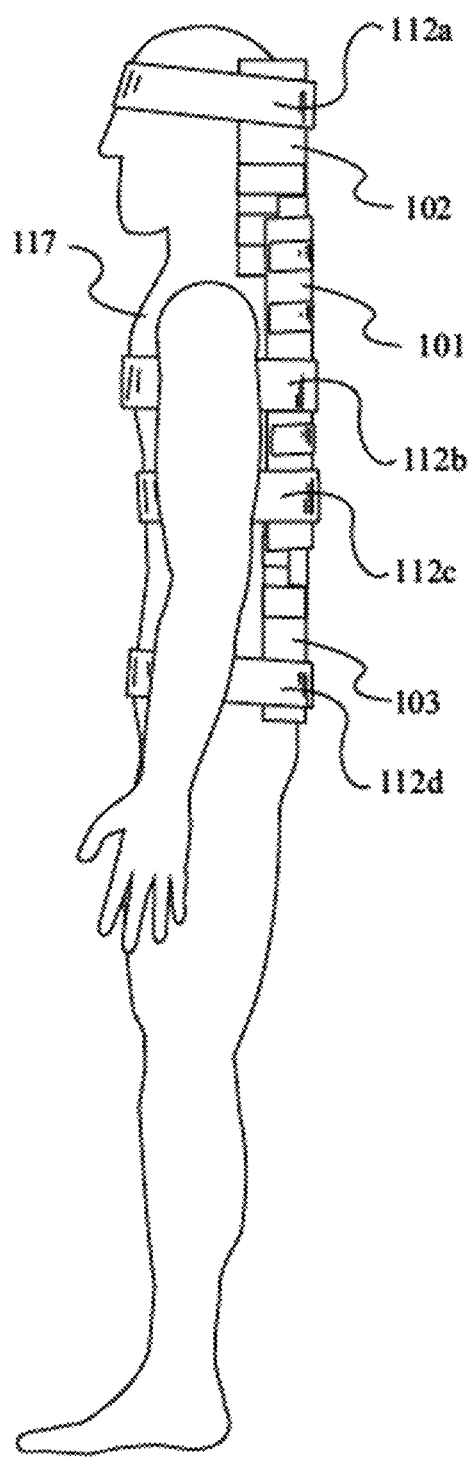
FIG. 4 is a side view of the first section with the additional second section of the embodiment depicted in FIG. 1A, deployed at one hundred and eighty degrees so as to support a neck and/or back of the subject in need thereof, as disclosed and described herein.

FIG. 4 is a side view of the first section (101) and the additional sections (102 and 103) deployed at one hundred and eighty degrees and held in place by straps (112a, 112b, 112c, and 112d) to support the neck and back of a body (117). In use, the various main and additional sections of the system may be used together to create a long rigid support, or used separately, or in any combination to create the required configuration to stabilize the injury or injuries presented to the first responder. First responders may be, for example, military medics or corpsmen, search and rescue team members, and emergency medical technicians.

Figure 5:
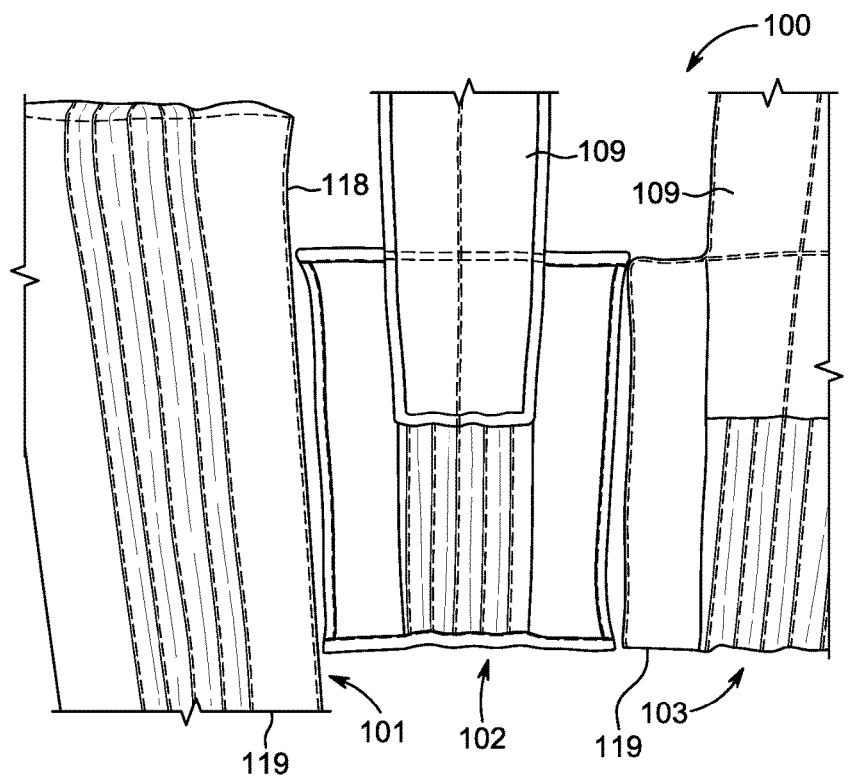
FIG. 5 is a top view digital photograph of exemplary components of the splint assembly as disclosed and described herein.
Figure 6:
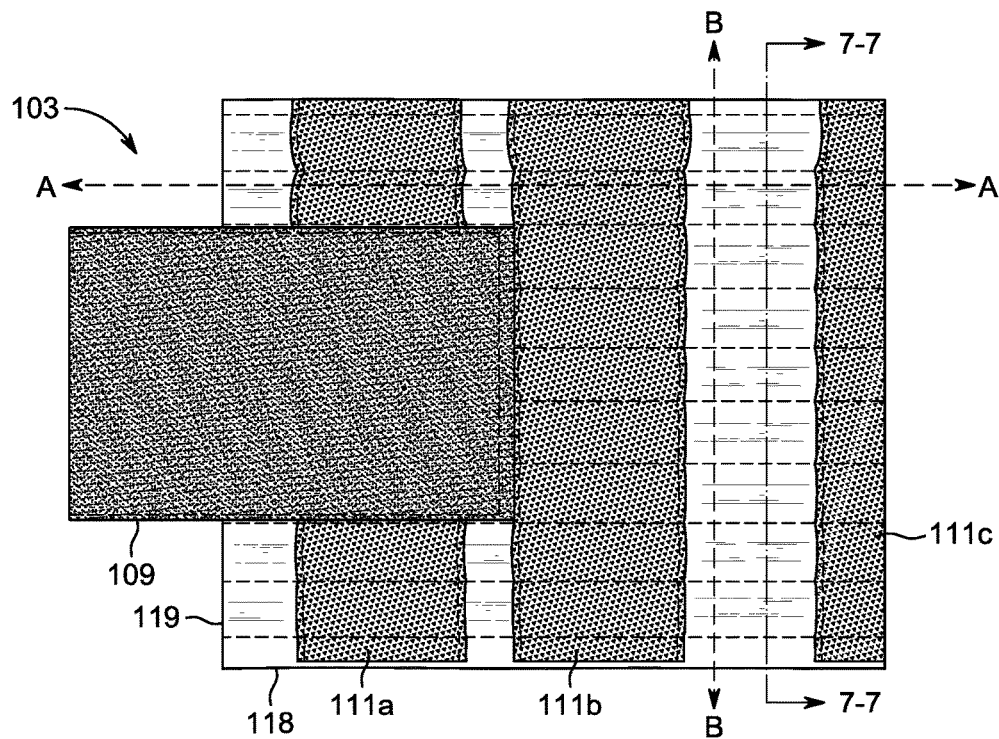
FIG. 6 is a top view digital photograph of an additional section of the splint assembly as disclosed and described herein.

FIG. 5 depicts a digital photograph of an exemplary splint assembly, showing disassembled first section (101), additional sections (102, 103). FIG. 6 depicts a digital photograph showing a top view of an additional section (103) showing loop connector material (111a, 111b, 111c) on surface (98).

The cover, the straps, and the hook and loop connector material may be natural or synthetic fabric based materials (woven or non-woven). Surfaces 98, 99 can be assembled by various stitching and/or bonding techniques to provide one or more compartments (106) configured to receive one or more rigid members (105). The straps may be an elastic and/or flexible material. Hook and loop connector material provides a strong and removable attachment that can be reused or adjusted many times without loss of efficacy.

Rigid members (105) may be held in place in the compartments (106) of the first and/or additional second sections (101, 102, 103), for example by sewn seams or VELCRO, or adhesive—which can be essentially permanent or reversibly sealed. In one aspect the rigid members are arranged in parallel to provide stiffness in one axis and flexibility in other axes. In one aspect the rigid members are arranged in parallel to provide stiffness in only one axis. The rigid members may be of various materials such as wood, metal (aluminum or stainless steel), or plastic. A common, inexpensive, stiff, and light weight material suitable for use may be wooden or plastic dowels. The rigid members can be of a length suitable for use for human appendages such as leg, arm, or spine. The rigid members can be of a cross section shape corresponding to the nature and construction of the rigid member itself, e.g., a wooden or plastic dowel of approximately ½ inch to 1 inch, or aluminum tubing or solid rod of ⅛ inch to about ½ inch. Other configurations of rigid members (105) and compartment (106), shapes, and/or materials can be employed, such as web-shapes or interlocking segments, etc. The one or more rigid members of the first section can be of a diameter and/or length and/or width that is/are different than at least one of the one or more rigid members of the second sections. In such configurations, the amount of conformity of the section can be controlled, e.g., more arc of curvature for a leg verses that of an arm or to accommodate the width of a foot and diameter of the corresponding ankle. Thus, the main section can be of a construction with longer and/or wider/thicker rigid members than the one or more second sections, for example.

Figure 7A:
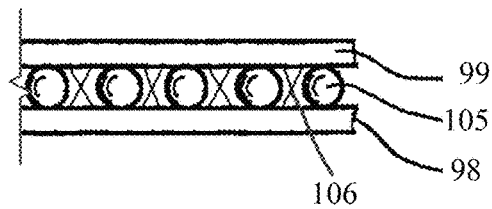
FIGS. 7A, 7B, 7C and 7D are cross-sectional views along sectional plane 7-7 of FIG. 6, depicting inflexible member configurations of the splint assembly as disclosed and described herein.
Figure 7B:
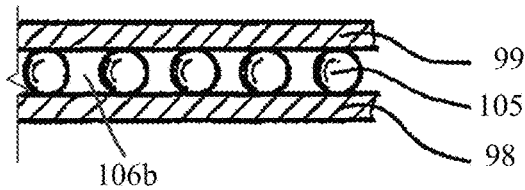
Figure 7C:
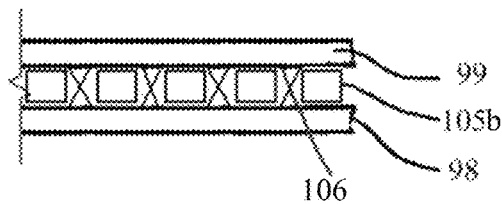
Figure 7D:
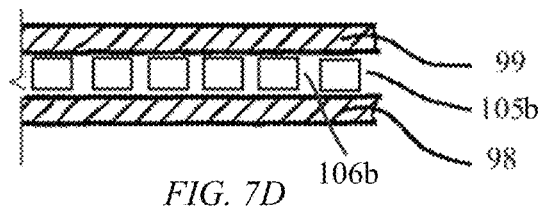

FIG. 7A depicts dowel-like rigid members (105) arranged in a plurality of individual compartments (106). FIG. 7B depicts dowel-like rigid members (105) arranged a single compartment (106b). FIGS. 7C and 7D depict rigid members (105) of a different geometric construction such as a straps or bands (as shown) which can be individual components or a single component.

Figure 8:
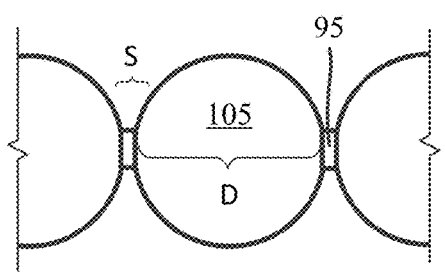
FIG. 8 depicts an alternate configuration of an inflexible member as disclosed and described herein.
Figure 9:
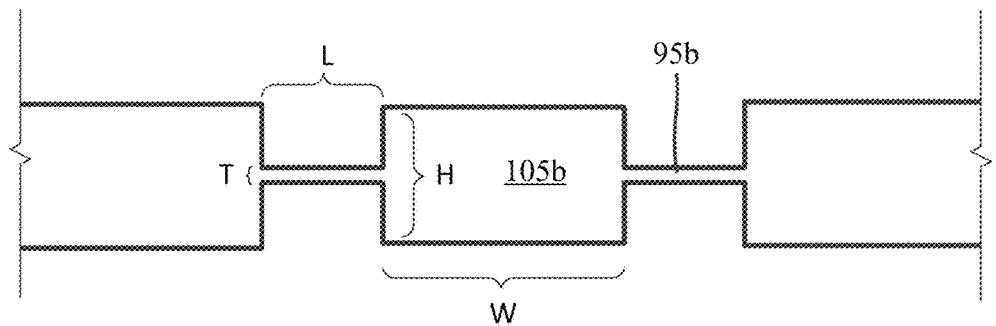
FIG. 9 depicts another alternate configuration of an inflexible member as disclosed and described herein.

FIG. 8 depicts an alternate configuration of rigid member (105) having dowel-like shape of diameter D spaced apart from adjacent rigid members by spacer (95) providing a space S. The diameter D and space S can be selected to accommodate the average human appendages and/or body. Spacer S can be a flexible material such as a foam or elastic and can be configured to accept the rigid member in a spacer compartment. Likewise, FIG. 9 depicts an alternative configuration of rigid member (105b) having a generally rectangular shape H and width W separated by spacer 95b of length L. Spacer 95b can be arranged with thickness T such that the rigid member has flexibility primarily about (in or out of) a plane including a single longitudinal axis of the rigid member so as to wrap around or otherwise at least partially conform to that of an appendage (leg, arm, hand, foot, neck) and/or body, and/or to be wrapped for compact storage. Thickness T can be a fraction of the height H, e.g., ½, ⅓, ¼, more or less, as desired and in accordance with the properties of the rigid member material. In this embodiment, suitable materials include flexible but rigid thermoplastics such as polypropylene, polyethylene copolymers, or ultra-high molecular weight polyethylene, for example. Such polymers can be filled with reinforcing materials, such reinforcing materials can be oriented or randomly distributed in the polymer to provide rigidity in substantially the longitudinal direction of the rigid member.

Longitudinal edges (118) can be permanently or reversibly sealed at one or both ends, for example, using Velcro, stitching, adhesives, etc. Likewise, longitudinal edges (118) can be permanently or reversibly sealed at one or both ends, for example, using Velcro, stitching, adhesives, etc., whereas cross-sectional edges (119) can be permanently sealed by stitching and/or adhesive bonding.

The splint assembly (100) can be provided with the one or more rigid members (105) separate from the first section (101) and additional sections (102, 103) so that the first responder can arrange the splint in a manner consistent with the injury. The one or more rigid members (105) can be inserted into the at least one compartment (106) and the cross-sectional edge (119) can be left open and/or sealed just prior to use. The surface of the one or more rigid members (105) can be manufactured or provided with a coefficient of friction relative to the interior surface of the one or more compartment (106) to resist and/or eliminate movement of the rigid member (105).

The splint assembly described herein may be quickly configured to effectively splint numerous types of breaks at various locations in the anatomy. The combination of a first section with repositionable additional sections fixed along a central axis allows for rapid change of length and easy creation of required angles for joint support. Independently position-able straps for fixing the device in place augment the versatility of the system.

The splint assembly described herein may be manufactured using conventional techniques or can be assembled by hand or combinations of hand/automation techniques known in the art to assembly fabric, provide compartments (e.g., sewing or bonding) therein and/or insert rigid members. The assembly provides a splint that can be quickly and easily be folded together and/or rolled up for transportation, minimizing the space it requires without the need for disassembly. The materials and methods of construction can be chosen so as to provide for a lightweight and durable system that allows for easy portability.

Of course, various changes, modifications and alterations in the teachings of the present disclosure may be contemplated by those skilled in the art without departing from the intended spirit and scope of the appended claims.

I claim:

1. A splint assembly comprising:
   a first section comprising:
      a top surface;
      an opposing bottom surface separated from the top surface by a peripheral edge; the peripheral edge comprising a pair of longitudinal edges and a pair of cross-sectional edges;
      at least one compartment positioned between the top surface and the bottom surface generally aligned with the longitudinal edges;
      one or more rigid members positioned within the at least one compartment, the one or more rigid members generally aligned with the longitudinal edges so that the first section has a rigid dimensional axis and at least one flexible dimensional axis;
   at least one second section configured to couple with the first section, each of the at least one second section comprising:
      a top surface;
      an opposing bottom surface separated from the top surface by a peripheral edge; the peripheral edge comprising a pair of longitudinal edges and a pair of cross-sectional edges;
      at least one compartment positioned between the top surface and the bottom surface generally aligned with the longitudinal edges;
      one or more rigid members positioned within the at least one compartment, the one or more rigid members generally aligned with the longitudinal edges so that the at least one second section has a rigid dimensional axis and at least one flexible dimensional axis;
      at least one attachment member having a first end and a second end, the at least one attachment member operatively coupled to at least one of the pair of cross-sectional edges of each of the at least one second section and configured for coupling with the top or the bottom surface of the first section or another of the at least one second sections; wherein the at least one attachment members of each of the at least one second section is reversibly repositionable along a central axis of the first section, the central axis complementary with the longitudinal edges of the first section, so as to allow for a change of length of the splint assembly; the combination of the first section and the at least one second section provides a splint assembly having a rigid dimensional axis and at least one flexible dimensional axis; and
      one or more elongated strap members, each of the one or more strap members having fastening means at opposing ends thereof, the fastening means reversibly couplable to the top or the bottom surface of the first section and the at least one second section.

2. The splint assembly of claim 1, wherein the at least one attachment member is fixedly coupled at the first or the second end to at least one of the pair of cross-sectional edges of the at least one second section and reversibly coupled to the top or the bottom surface of another one of the first section or another of the at least one second sections.

3. The splint assembly of claim 1, wherein two of the at least one second section are reversibly repositionable to the top surface or the opposing bottom surface of the first section by fastening members.

4. The splint assembly of claim 3, wherein the rigid dimensional axis of the one or more second section is configure to articulate about the fastening members between an angle of zero to 180 degrees relative to the rigid dimensional axis of the first section.

5. The splint assembly of claim 3, wherein the fastening members of two of the at least one second section are coupled to the proximity of the opposing cross-sectional edges of the first section to provide an extended elongated structure consisting of the first section and the two of the at least one second sections.

6. The splint assembly of claim 3, wherein the fastening members of two or more of the one or more second sections are coupled in proximity to opposing cross-sectional edges of two or more of the at least one second section.

7. The splint assembly of claim 1, wherein the first section comprises a number of the one or more rigid members less than that of the at least one second sections.

8. The splint assembly of claim 1, wherein the one or more rigid members of the first section are of a diameter and/or length that is different than at least one of the one or more rigid members of the second sections.

9. The splint assembly of claim 1, wherein the elongated flexible sections provide an extended elongated structure that is of a length corresponding to that of at least a portion of a human arm, or of a length corresponding to that of at least a portion of a human leg, or of a length corresponding to that of at least a portion of a human spine.

10. A method of manufacturing a splint assembly, the method comprising:
   providing a first section comprising:
      a top surface;
      an opposing bottom surface separated from the top surface by a peripheral edge; the peripheral edge comprising a pair of longitudinal edges and a pair of cross-sectional edges;
   forming at least one compartment positioned between the top surface and the bottom surface generally aligned with the longitudinal edges; the at least one compartment configured to receive or more rigid members generally aligned with the longitudinal edges so that the first section has a rigid dimensional axis and at least one flexible dimensional axis;
   providing at least one second section configured to reversibly and repositionally couple with the first section, each of the at least one second section comprising:
      a top surface;
      an opposing bottom surface separated from the top surface by a peripheral edge; the peripheral edge comprising a pair of longitudinal edges and a pair of cross-sectional edges;
      forming at least one compartment positioned between the top surface and the bottom surface generally aligned with the longitudinal edges; the at least one compartment configured to receive one or more rigid members generally aligned with the longitudinal edges so that the at least one second section has a rigid dimensional axis and at least one flexible dimensional axis; and
      providing at least one attachment member having at least one end operatively coupled to at least one of the pair of cross-sectional edges of each of the at least one second section and configured for reversible and repositionable coupling with the first section, or another of the at least one second sections;
   whereby the first section and the at least one second section is configurable as a splint assembly having a rigid dimensional axis and at least one flexible dimensional axis.

11. The method of claim 10, wherein the at least one attachment member is fixedly coupled at the first or the second end to at least one of the pair of cross-sectional edges of the at least one second section and reversibly and repositionally coupled to the top or the bottom surface of the first section, or another of the at least one second sections.

12. The method of claim 10, wherein the at least one compartment is configured to be reversibly sealed with the one or more rigid member or irreversibly sealed with the one or more rigid member.

13. The method of claim 10, wherein the rigid dimensional axis of the one or more second section is configured to articulate about the at least one attachment members between an angle of zero to 180 degrees relative to the rigid dimensional axis of the first section.

14. The method of claim 10, wherein the at least one attachment members of two of the at least one second section are coupled in proximity of the opposing cross-sectional edges of the first section.

15. The method of claim 10, wherein the one or more rigid members is a rod, sheet, or strip of material.

16. The method of claim 10, further comprising providing one or more elongated strap members, each of the one or more elongated strap members having fastening means at opposing ends thereof, the fastening means configured for reversibly coupling to the top or the bottom surface of the first section and/or the at least one second section.

17. A splint assembly comprising:
a first section comprising:
at least one compartment positioned between a top surface and a bottom surface;
one or more rigid members positioned within the at least one compartment, so that the first section has a rigid dimensional axis and at least one flexible dimensional axis;
at least one second section configured to couple with the first section comprising: at least one compartment positioned between a top surface and a bottom surface;
one or more rigid members positioned within the at least one compartment so that the at least one second section has a rigid dimensional axis and at least one flexible dimensional axis;
at least one attachment member operatively couplable to the first section or another of the at least one second sections; wherein the at least one attachment member of each of the at least one second section is reversibly repositionable along a central axis of the first section, the central axis complementary with the longitudinal edges of the first section, so as to allow for a change of length of the splint assembly; and
one or more elongated strap members, each of the one or more elongated strap members having fastening means at opposing ends thereof, the fastening means reversibly couplable to the first section and the at least one second section;
wherein the combination of the first section and the at least one second section provides a splint assembly having a rigid dimensional axis and at least one flexible dimensional axis.

18. The splint assembly of claim 17, wherein the rigid member is a rod, sheet, or strip of material.

* * * * *